(12) United States Patent
Loreth

(10) Patent No.: US 10,537,338 B2
(45) Date of Patent: Jan. 21, 2020

(54) ARTHROSCOPIC RESECTION METHODS

(71) Applicant: Smith & Nephew, Inc., Memphis, TN (US)

(72) Inventor: Brian J. Loreth, Braintree, MA (US)

(73) Assignee: Smith & Nephew, Inc., Memphis, TN (US)

( * ) Notice: Subject to any disclaimer, the term of this patent is extended or adjusted under 35 U.S.C. 154(b) by 324 days.

(21) Appl. No.: 15/449,553

(22) Filed: Mar. 3, 2017

(65) Prior Publication Data

US 2017/0181754 A1    Jun. 29, 2017

Related U.S. Application Data

(60) Continuation of application No. 13/860,464, filed on Apr. 10, 2013, now Pat. No. 9,622,756, which is a
(Continued)

(51) Int. Cl.
*A61B 17/16* (2006.01)
*A61B 17/32* (2006.01)

(52) U.S. Cl.
CPC .......... *A61B 17/16* (2013.01); *A61B 17/1615* (2013.01); *A61B 17/1631* (2013.01); *A61B 17/1633* (2013.01); *A61B 17/32002* (2013.01); *A61B 17/1628* (2013.01); *A61B 17/1662* (2013.01); *A61B 2017/1602* (2013.01)

(58) Field of Classification Search
CPC . A61B 17/16; A61B 17/1604; A61B 17/1615; A61B 17/1637; A61B 17/1659; A61B 17/32003; A61B 17/3207; A61B 13/320758; A61B 17/320775; A61B 17/1631; A61B 17/1633; A61B 17/32002;
(Continued)

(56) References Cited

U.S. PATENT DOCUMENTS 5,047,040 A * 9/1991 Simpson ............ A61B 17/3207
604/22
5,759,185 A * 6/1998 Grinberg ............ A61B 17/1615
606/180

(Continued)

FOREIGN PATENT DOCUMENTS

DE    8418723 U    9/1984
DE    19639193 A1    4/1998
(Continued)

OTHER PUBLICATIONS

International Search Report, PCT/US2011/029708, dated Aug. 29, 2011, pp. 5.
(Continued)

*Primary Examiner* — Kathleen S Holwerda

(57) ABSTRACT

The present disclosure relates to resection devices and methods. The resection device includes an outer tubular member; and an inner tubular member disposed within the outer tubular member, the inner tubular member including a burr having a body with flutes extending along a length of the body, the flutes including parabolic wave patterns located along surface edges of the flutes. In an embodiment, the parabolic wave patterns extend along entire lengths of the flutes. Other resection devices and methods are also disclosed.

16 Claims, 3 Drawing Sheets

Related U.S. Application Data division of application No. 13/070,584, filed on Mar. 24, 2011, now abandoned.

(60) Provisional application No. 61/443,301, filed on Feb. 16, 2011, provisional application No. 61/316,860, filed on Mar. 24, 2010.

(58) Field of Classification Search
CPC ............ A61B 16/1628; A61B 17/1662; Y10T 407/1958; Y10T 408/907
See application file for complete search history.

(56) References Cited

U.S. PATENT DOCUMENTS

| | | | |
|---|---|---|---|
| 5,913,867 | A | 6/1999 | Dion |
| 6,045,305 | A | 4/2000 | Plummer |
| 6,258,093 | B1 | 7/2001 | Edwards |
| 6,419,684 | B1 | 7/2002 | Heisler et al. |
| 7,207,752 | B2 * | 4/2007 | Schulte .................. B23D 77/00 408/1 R |
| 2002/0090273 | A1 | 7/2002 | Serwa |
| 2005/0283160 | A1 | 12/2005 | Knisely et al. |
| 2008/0132929 | A1 * | 6/2008 | O'Sullivan ........ A61B 17/1615 606/170 |
| 2008/0140078 | A1 | 6/2008 | Nelson et al. |
| 2009/0048602 | A1 | 12/2009 | O'Donoghue |
| 2010/0312338 | A1 | 12/2010 | Gonzales et al. |
| 2011/0015667 | A1 | 1/2011 | Gonzales et al. |
| 2011/0015734 | A1 | 1/2011 | Gonzales et al. |
| 2011/0022172 | A1 | 1/2011 | Gonzales et al. |

FOREIGN PATENT DOCUMENTS

| | | |
|---|---|---|
| WO | 199827876 A1 | 7/1998 |
| WO | 2007142830 A2 | 12/2007 |
| WO | 2008145380 A1 | 12/2008 |
| WO | 2010141850 | 12/2010 |

OTHER PUBLICATIONS

EPO Second Office Action, Application No. 11714167.1-1654, Applicant Smith & Nephew, dated Jan. 21, 2015.
Australian Patent Examination Report No. 1 dated Apr. 7, 2015 for Australian Patent Application No. 2011232446 (Note all references listed in Examination Report previously identified by Applicants).
Notice of Reasons for Rejection, Japanese Application No. 2013-501441, dated May 25, 2015.
Second Office Action State Intellectual Property Office, P.R. China for Chinese Application No. 201180015765, dated Oct. 14, 2015 (D1 and D2 previously cited).
Australian Patent Examination Report No. 2, Patent Application No. 2011232446, dated Dec. 4, 2015 (D1 and D2 previously cited).
Office Action for Canadian Patent Application No. 2,759,817, dated Jan. 20, 2016.
India Examination Report—Application No. 8312/DELNP/2012 dated Jul. 26, 2019.

* cited by examiner

ARTHROSCOPIC RESECTION METHODS

CROSS-REFERENCE TO RELATED APPLICATIONS

This application is a continuation of U.S. application Ser. No. 13/860,464 filed Apr. 10, 2013 titled "Arthroscope Resection Methods." The Ser. No. 13/860,464 application was a divisional of U.S. application Ser. No. 13/070,584 filed Mar. 24, 2011 titled "Arthroscopic Resection Devices," which claimed benefit of U.S. Provisional Application No. 61/316,860 filed Mar. 24, 2010 and U.S. Provisional Application No. 61/443,301 filed Feb. 16, 2011. All the noted applications are incorporated by reference herein as if reproduced in full below.

TECHNICAL FIELD

The present disclosure relates to arthroscopic resection devices and methods for resection of tissue.

BACKGROUND

Arthroscopic resection devices have been used in performing closed surgery, such as endoscopic surgery, i.e. arthroscopic surgery. Generally, these devices include, without limitation, blade devices and burr devices. Both the blade and burr devices include an elongate outer tubular member terminating at a distal end having an opening in the side wall and/or the end wall to form a cutting port or window. Both devices also include an elongate inner tubular member coaxially disposed in the outer tubular member and having a distal end disposed adjacent the port/window in the distal end of the outer tubular member. The distal end of the inner tubular member of the blade device has a surface or edge for engaging tissue via the port/window in the distal end of the outer tubular member and in many cases cooperates with the port/window to shear or cut tissue. Alternatively, the distal end of the inner tubular member of the of the burr device has a burr having helical grooved surfaces or flutes for drilling and grinding tissue via the port/window in the distal end of the outer tubular member and in many cases cooperates with the port/window to shear or cut tissue. The inner tubular members are rotatably driven at their proximal ends, normally via a hand piece having a small electric motor therein controlled by finger-actuated switches on the hand piece. A foot switch or switches on a console supply power to the hand piece.

The helical flutes of the burr tend to not have any additional distinguishing geometrical features designed to enhance performance. They typically have smooth, non-serrated cutting edges and follow the design of end mills or drills. Additionally, the burrs tend to have the same number of flutes along the entire body of the burr. The surfaces or edges of the blade device inner member typically have straight cutting edges.

The characteristics of these cutting features result in a less aggressive cutting action, thereby resecting the tissue or bone into larger fragments that increase the chances of the device becoming clogged, as well as cloud the image a surgeon has inside the surgical area. Additionally, these characteristics increase the possibility of the device displaying unpleasant harmonics or resonance during use. Furthermore, having the same number of flutes along the body of the burr allows for only one style of cutting, thereby providing the burr device with less versatility. Therefore, arthroscopic resection devices that alleviate these limitations are needed.

SUMMARY

In an aspect, the present disclosure relates to a resection device. The resection device includes an outer tubular member; and an inner tubular member disposed within the outer tubular member, the inner tubular member including a burr having a body with flutes extending along a length of the body, the flutes including parabolic wave patterns located along surface edges of the flutes. In an embodiment, the parabolic wave patterns extend along entire lengths of the flutes.

In another aspect, the present disclosure relates to a resection device. The resection device includes an outer tubular member; and an inner tubular member disposed within the outer tubular member, the inner tubular member including a burr having a body with flutes extending along a length of the body and a tip with flutes, wherein the tip and the body include a different number of flutes. In an embodiment, the body has a higher number of flutes than the tip. In another embodiment, the body has a lower number of flutes than the tip.

In yet another embodiment, the flutes on either the body or the tip include parabolic wave patterns located along surface edges of the flutes. In a further embodiment, the device further includes a transition piece located between the inner tubular member and the burr, the transition piece including a proximal portion and a tapered distal portion. In yet a further embodiment, the device further includes an opening located between the inner tubular member and the burr. In an embodiment, the opening leads to a passageway, the passageway extending along a length of the inner tubular member.

In yet another aspect, the present disclosure relates to a resection device. The resection device includes an outer tubular member; and an inner tubular member disposed within the outer tubular member, the inner tubular member including a burr having a body with flutes extending along a length of the body and a tip with flutes, wherein the tip and the body include a different number of flutes, the flutes on either the body or the tip including parabolic wave patterns located along surface edges of the flutes.

In still another aspect, a surgical method is disclosed that includes providing an arthroscopic resection device including an outer tubular member, and an inner tubular member disposed within the outer tubular member. The inner tubular member includes an arthroscopic burr having a body with flutes extending along a length of the body and a tip with flutes, such that the tip and the body include a different number of flutes. The surgical method further includes performing an arthroscopic resection procedure on target tissue using the arthroscopic resection device.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION

The disclosures of U.S. patent application Ser. No. 13/860,464 filed Apr. 10, 2013, U.S. patent application Ser. No. 13/070,564 filed Mar. 24, 2011, U.S. Provisional Patent Application No. 61/316,860 filed Mar. 24, 2010, and U.S. Provisional Patent Application No. 61/443,301 filed Feb. 16, 2011, are hereby incorporated herein by reference in their entirety as if reproduced in full below.

The following description of the preferred embodiment(s) is merely exemplary in nature and is in no way intended to limit the disclosure, its application, or uses.

Figure 1:
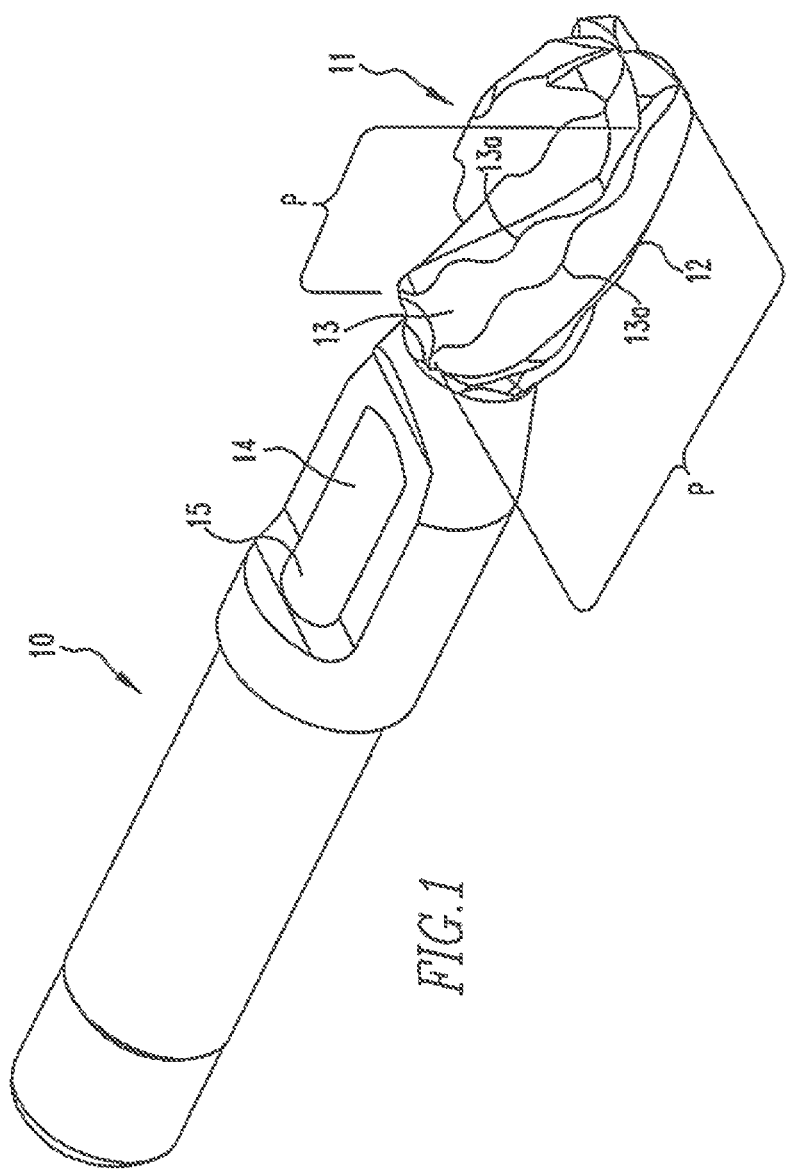
FIG. 1 shows a first embodiment of an inner tubular member of the present disclosure.
Figure 2:
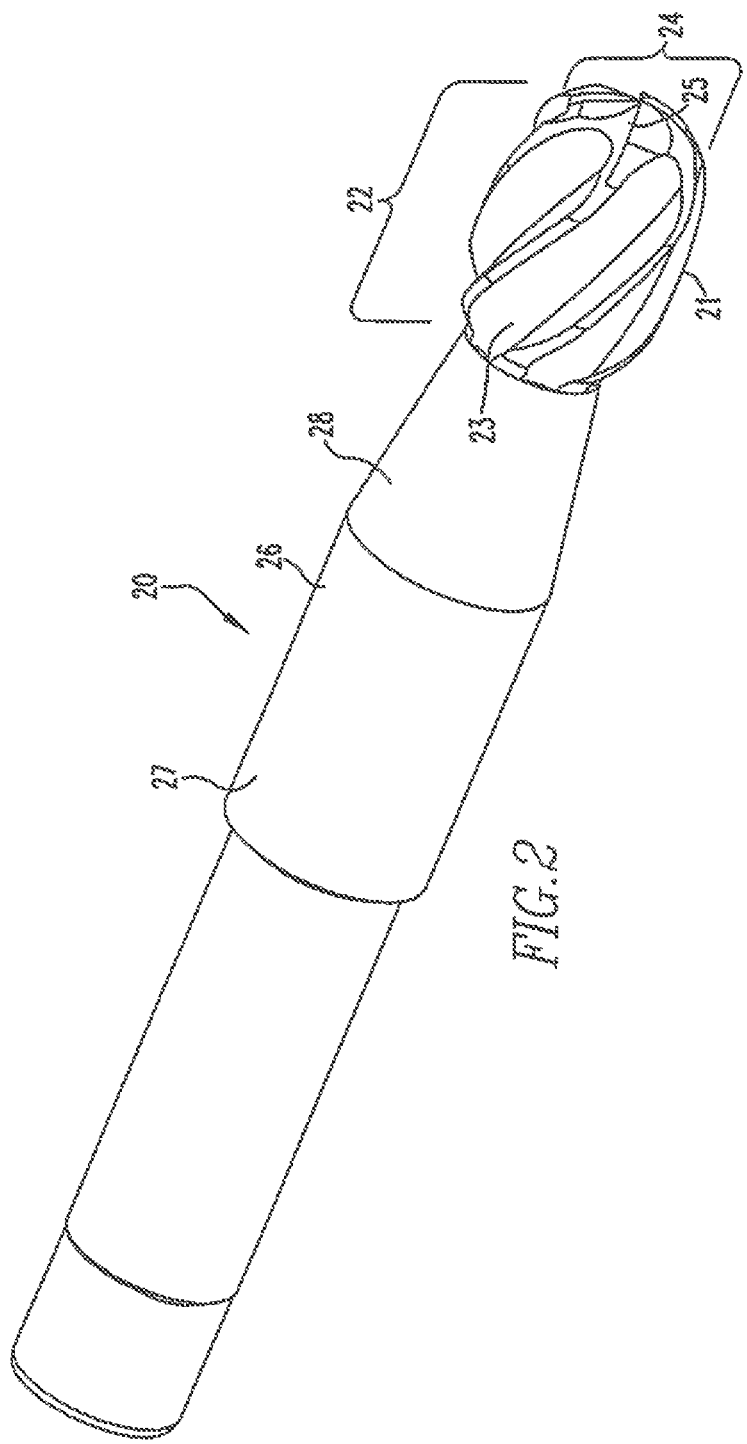
FIG. 2 shows a second embodiment of an inner tubular member of the present disclosure.
Figure 3:
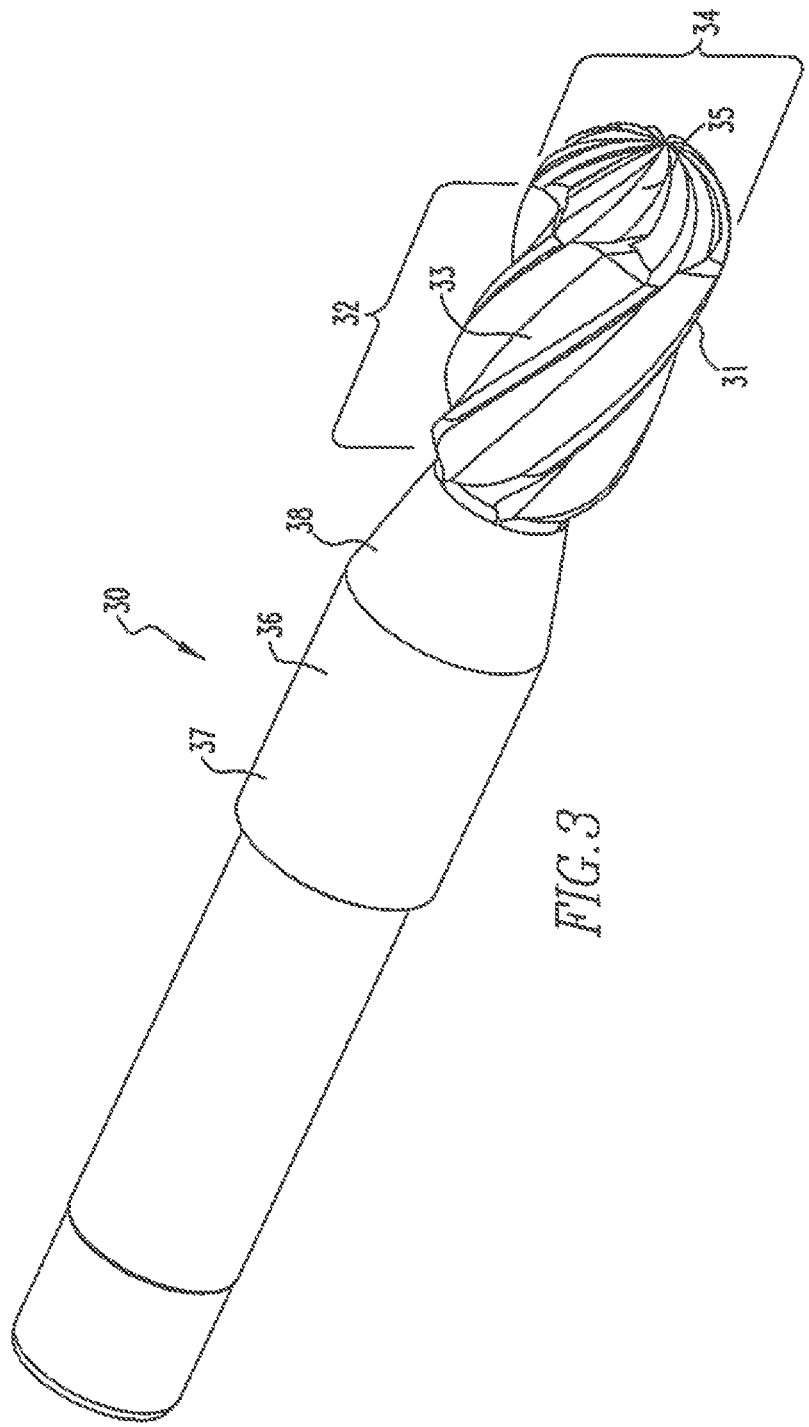
FIG. 3 shows a third embodiment of an inner tubular member of the present disclosure.

FIGS. 1-3 show inner tubular members for use with burr devices and, specifically, the distal ends of the members. FIG. 1 shows an inner tubular member 10 including a burr 11 having a body 12 with helical flutes 13 extending along the length of the body 12. The surface edges 13a of the flutes 13 incorporate parabolic wave patterns P along the entire lengths of the flutes 13. The burr 11 may have any number of flutes 13 and the flutes 13 may be located at any angle relative to a longitudinal axis passing through the burr 11. Additionally, the flutes 13 may incorporate a pattern having an alternate geometry that may not be truly parabolic, but has the cutting characteristics of the parabolic wave pattern.

Located proximal to the burr 11 and between the inner tubular member 10 and the burr 11 is an opening 14 to a passageway 15 extending the length of the inner tubular member 10. The passageway 15 allows for the flow of fragmented tissue and bone during surgery. A vacuum (not shown) is attached to a proximal end (not shown) of the member 10 for vacuuming the tissue through the passageway 15.

The parabolic wave patterns P on the flutes 13 provide the burr 11 with a more aggressive cutting action, especially when used in cutting bone, which causes the burr 11 to cut the bone into smaller fragments. Having smaller bone fragments allows the fragments to be removed more readily by the vacuum, thereby reducing the possibility of clogging and obscuring the visual image of the surgical area. Additionally, the parabolic wave pattern P deliberately creates inconsistencies in the burr geometry, thereby lessening any unpleasant harmonics or resonance of the burr device. This lessening, coupled with the fact the pattern P yields constant acceleration, provides the device with smoother cutting performance and controllability.

FIG. 2 shows another inner tubular member 20 including a burr 21 having a body 22 with helical flutes 23 extending along the length of the body 22 and a tip 24 also having helical flutes 2. The tip 24 has a lower number of flutes 25 than the body 22. Having a lower number of flutes 25 on the tip 24 makes the tip 24 cut more aggressively than the body 22 because the individual cutting area of each flute 25 is more. FIG. 3 shows yet another inner tubular member 30 including a burr 31 having a body 32 with helical flutes 33 extending along the length of the body 32 and a tip 34 with helical flutes 35. Unlike member 20, the tip 34 of burr 31 has a higher number of flutes 35 than the body 32. Having a higher number of flutes 35 on the tip 34 makes the tip 34 cut less aggressively than the body 32 because the individual cutting area of each flute 35 is less.

Having a transitional fluted burr with a different number of flutes on the tip than on the body provides more versatility to the user. The ability to perform different cutting techniques with one burr is more efficient than using two different devices. Additionally, it is more cost effective to use this type of burr due to only one burr having to be inventoried and utilized.

Any different number combination of flutes may be used on the burrs 21,31 and the flutes 23,25,33,35 may be located at any angle relative to a longitudinal axis passing through the burr 21,31. Additionally, it is within the scope of this disclosure to have parabolic wave patterns along the lengths of any of the flutes 23,25,33,35, similar to the wave patterns P on flutes 13. The patterns may be located on the surface edges of the flutes 23,25,33,35 and along the entire length or along a partial length of the flutes 23,25,33,35. Furthermore, it is within the scope of this disclosure to have an alternating number of flutes having the wave patterns. Even further, the flutes 23,25,33,35 may incorporate a pattern having an alternate geometry that may not be truly parabolic, but has the cutting characteristics of the parabolic wave pattern.

Both burrs 21,31 are coupled to transition pieces 26,36 located between the inner tubular members 20,30 and the burrs 21,31. The transition pieces 26,36 include proximal portions 27,37 and tapered distal portions 28,38. In use, all of the members 10,20,30 would be disposed within an outer tubular member, as discussed above.

The inner tubular members 10,20,30 and their components are made from metal material. However, other material strong enough to withstand the forces of a tissue cutting action may be used. The flutes, parabolic wave patterns on the flutes, and opening are made via a machining process or other process known to those of skill in the art.

As various modifications could be made to the exemplary embodiments, as described above with reference to the corresponding illustrations, without departing from the scope of the disclosure, it is intended that ail matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An arthroscopic resection device for arthroscopic surgery comprising:
an outer tubular member;
an inner tubular member disposed within the outer tubular member and extending along and rotatable about a rotational axis;
a burr disposed at a distal end of the inner tubular member, the burr having a body extending axially to a distal tip;
a plurality of flutes each having a length extending axially along and around the body, each flute extends radially to a radial periphery, each flute defines a first surface extending along the length and radially to the radial periphery and a second surface opposite the first surface, the second surface extending along the length and radially to the radial periphery, the first surface and second surface being spaced from one another to define a thickness of each of the plurality of flutes, wherein the first and second surfaces extend along the length to define first and second parabolic wave patterns, respectively, and wherein the thickness varies in a lengthwise direction along at least a portion of the length as a result of the first and second parabolic wave patterns.

2. The arthroscopic resection device of claim 1 wherein the first parabolic wave pattern of the first surface of each flute extends along an entirety of the length of each flute.

3. The arthroscopic resection device of claim 1 wherein the second parabolic wave pattern of the second surface of each flute extends along an entirety of the length of each flute.

4. The arthroscopic resection device of claim 1 wherein the plurality of flutes are helical with respect to a rotational axis of the burr.

5. The arthroscopic resection device of claim 1 further comprising a plurality of flutes on the distal tip.

6. The arthroscopic resection device of claim 5 wherein a number of the plurality of flutes on the body is greater than a number of the plurality of flutes on the distal tip.

7. The arthroscopic resection device of claim 5 wherein a number of the plurality of flutes on the body is the same as a number of the plurality of flutes on the distal tip.

8. The arthroscopic resection device of claim 5 wherein a number of the plurality of flutes on the body is less than a number of the plurality of flutes on the distal tip.

9. The arthroscopic resection device of claim 5 wherein:
each flute on the distal tip defines a first edge and a second edge opposite the first edge of each flute on the distal tip; and
at least a portion of the first edge of each flute on the distal tip defines a parabolic wave pattern.

10. The arthroscopic resection device of claim 9 wherein at least a portion of the second edge of each flute on the distal tip defines a parabolic wave pattern.

11. An arthroscopic resection device for arthroscopic surgery comprising:
an outer tubular member;
an inner tubular member disposed within the outer tubular member;
a burr disposed at a distal end of the inner tubular member, the burr having a body extending axially to a distal tip;
a first plurality of flutes each having a length extending axially along and around the body of the burr, each flute of the first plurality of flutes extends radially to a radial periphery, each flute of the first plurality of flutes defines a first edge and a second edge opposite the first edge, the first and second edges each extending along the length and radially to the radial periphery, at least a portion of the first edge of each flute of the first plurality of flutes defines a first parabolic wave pattern, and at least a portion of the second edge of each flute of the first plurality of flutes defines a second parabolic wave pattern, wherein the first and second edges being spaced from one another to define a thickness varying in a lengthwise direction along at least a portion of the length as a result of the first and second parabolic wave patterns;
a second plurality of flutes on the distal tip, each flute of the second plurality of flutes defines a third edge and a fourth edge opposite the third edge, at least a portion of the third edge of each flute of the second plurality of flutes on the distal tip defines a third parabolic wave pattern, and at least a portion of the fourth edge of each flute of the second plurality of flutes on the distal tip defines a fourth parabolic wave pattern.

12. The arthroscopic resection device of claim 11 wherein at least one of the first parabolic wave pattern and the second parabolic wave pattern of each flute of the first plurality of flutes extends along an entirety of the length of each flute of the first plurality of flutes.

13. The arthroscopic resection device of claim 11 wherein the first plurality of flutes are helical with respect to a rotational axis of the burr.

14. The arthroscopic resection device of claim 11 wherein the first plurality of flutes has a greater number of flutes than a number of flutes of the second plurality of flutes.

15. The arthroscopic resection device of claim 11 wherein the first plurality of flutes has a lesser number of flutes than a number of flutes of the second plurality of flutes.

16. The arthroscopic resection device of claim 11 wherein the first plurality of flutes has a number of flutes equal to a number of flutes of the second plurality of flutes.

* * * * *